US005693319A

United States Patent [19]

Tremont

[11] Patent Number: 5,693,319
[45] Date of Patent: Dec. 2, 1997

[54] POLYAMINES AND METHOD FOR PREPARATION THEREOF

[75] Inventor: Samuel J. Tremont, Manchester, Mo.

[73] Assignee: Monsanto Company, St. Louis, Mo.

[21] Appl. No.: 399,312

[22] Filed: Mar. 6, 1995

Related U.S. Application Data

[60] Division of Ser. No. 976,990, Jan. 15, 1993, Pat. No. 5,474,767, which is a continuation of PCT/US91/05147, Jul. 22, 1991, which is a continuation-in-part of Ser. No. 558,041, Jul. 26, 1990, abandoned.

[51] Int. Cl.⁶ .................................................. C08F 8/32
[52] U.S. Cl. .................... 424/78.27; 424/78.17; 525/326.1; 525/331.7; 525/333.2; 525/379; 525/923
[58] Field of Search ................ 424/70.1, 78.17, 424/78.27; 529/326.1, 331.7, 333.2, 379, 923

[56] References Cited

U.S. PATENT DOCUMENTS

| | | | |
|---|---|---|---|
| 2,923,662 | 2/1960 | Markus et al. | 167/55 |
| 3,383,426 | 5/1968 | Cull et al. | |
| 4,068,056 | 1/1978 | Engel et al. | |
| 4,110,432 | 8/1978 | Wilkinson et al. | 424/85 |
| 4,228,152 | 10/1980 | Ferriti et al. | 424/81 |
| 4,292,242 | 9/1981 | Laine | |
| 4,297,481 | 10/1981 | Jachimowicz et al. | |
| 4,312,965 | 1/1982 | Jachinowicz et al. | |
| 4,356,166 | 10/1982 | Peterson et al. | 424/19 |
| 4,459,310 | 7/1984 | Dajanil et al. | 424/305 |
| 4,503,217 | 3/1985 | Alexander | |
| 4,526,936 | 7/1985 | Jachimowicz et al. | |
| 4,543,411 | 9/1985 | Knifton et al. | |
| 4,548,955 | 10/1985 | Okahata et al. | 521/53 |
| 4,558,101 | 12/1985 | Jachimowicz et al. | |
| 4,606,939 | 8/1986 | Frank et al. | 427/213.3 |
| 4,608,278 | 8/1986 | Frank et al. | 427/213.3 |
| 4,639,366 | 1/1987 | Heller | 424/19 |
| 4,657,984 | 4/1987 | McEntire et al. | |
| 4,663,308 | 5/1987 | Saffran et al. | 514/3 |
| 4,675,182 | 6/1987 | Strcuff et al. | 424/80 |
| 4,705,898 | 11/1987 | McEntire et al. | |
| 4,764,364 | 8/1988 | Heller et al. | 424/78 |
| 4,765,973 | 8/1988 | Heller | 424/486 |
| 4,780,318 | 10/1988 | Appelgren et al. | 424/469 |
| 4,780,319 | 10/1988 | Zentner et al. | 424/476 |
| 4,794,199 | 12/1988 | Lin et al. | |
| 4,795,436 | 1/1989 | Robinson | 424/422 |
| 4,814,176 | 3/1989 | Makino et al. | 424/457 |
| 4,847,250 | 7/1989 | Alexander et al. | 514/247 |
| 4,931,288 | 6/1990 | Embrey et al. | 424/486 |
| 5,049,625 | 9/1991 | Tazuma et al. | |
| 5,134,200 | 7/1992 | Wideman | |
| 5,434,309 | 7/1995 | McGrath et al. | |

FOREIGN PATENT DOCUMENTS 457 386 A2  11/1991  European Pat. Off.

OTHER PUBLICATIONS

Jachimowicz, F. et al., "Scope and Pathway of Catalytic Aminomethylation of Olefins", *J. Org. Chem.* 47, 445–47 (Jan. 1982).

Jachimowicz, F., et al., "Aminomethylation of Diene Polymers—Novel Route to Polyamines", Catalysis of Organic Reactions, Chemical Industries/22, Augustine, R.L. (ed), pp. 381–390 (Sep. 1985).

*Primary Examiner*—Edward J. Webman
*Attorney, Agent, or Firm*—Fitzpatrick, Cella, Harper & Scinto

[57] ABSTRACT

Cross-linked controlled density polyamines which are water-insoluble and swell at pH values up to about 8 are shown. These polyamines are useful in site-specific drug delivery systems.

3 Claims, 3 Drawing Sheets

POLYAMINES AND METHOD FOR PREPARATION THEREOF

BACKGROUND OF THE INVENTION

This application is a divisional of U.S. Ser. No. 07/976,990 filed Jan. 15, 1993, now U.S. Pat. No. 5,474,767, which is a continuation of application Ser. No. PCT/US91/05147 filed Jul. 22, 1991 which is a continuation-in-part of application Ser. No. 07/558,041 filed Jul. 26, 1990, now abandoned.

1. Field of the Invention

The present invention relates to functionalized polymeric materials and, more particularly, relates to water insoluble controlled density polyamines which are cross-linked. The subject polyamines swell at pH values of about 8 or less but do not swell at pH values above about 8. In addition, such polyamines can be functionalized to modify the properties thereof. For example, the polyamines can be quaternized rendering the polymeric material swellable at pH values greater than about 8, and/or a drug can be attached to such polyamines.

2. Related Art

It is well known in the art to convert olefins to aldehydes having one additional carbon atom by contacting a $C_2$ to $C_{20}$ monoolefin or a $C_5$ to $C_{5000}$ nonconjugated polyolefin with hydrogen and carbon monoxide in the presence of a catalyst based on cobalt or rhodium metal. See, for example, U.S. Pat. No. 4,871,878.

It is also known, as disclosed in U.S. Pat. No. 3,383,426, to hydroformylate polymers utilizing hydrocarbon-soluble phosphine and phosphite catalyst complexes which include a Group VIII transition metal and at least one ligand consisting of a carbon monoxide molecule.

The principle of obtaining amines starting from an olefin, hydrogen carbon monoxide and a primary or secondary amine is known. Various techniques embodying this principle have been described using catalysts of various kinds. Such techniques are generally referred to as aminomethylation reactions.

Helvetica Chemical Acta, Volume 53, pages 1440 to 1445 (1971) U.S. Pat. No. 3,947,458 (1976), teach catalytic aminomethylation of olefins employing a rhodium oxide catalyst, an iron carbonyl catalyst and a mixed rhodium oxide/iron carbonyl catalyst.

U.S. Pat. No. 4,096,150 (1978) discloses a process for the manufacture of tertiary amines wherein an olefin, hydrogen, CO and secondary amine are reacted in the presence of a coordination complex catalyst of a Group VIII metal and a ligand, the donor atom of which is oxygen, nitrogen or sulfur.

Amines can be prepared from a dehydrogenated paraffin feedstock reacted with a nitrogen-containing compound, carbon monoxide and hydrogen in the presence of a rhodium or ruthenium-containing compound. See U.S. Pat. No. 4,179,469.

It is known to prepare tertiary amines by reacting a long-chain olefin with carbon monoxide, hydrogen and a primary or secondary amine in the presence of a catalyst comprising rhodium and/or ruthenium and using a specifically outlined solvent which allows for phase separation. See U.S. Pat. Nos. 4,448,996 and 4,250,115.

U.S. Pat. No. 4,207,260 (1980) to Imai discloses tertiary amines prepared by reacting an aldehydes, hydrogen and a nitrogen-containing compound in the presence of rhodium or ruthenium-containing catalyst at temperatures in the range of 50°–350° F. and a pressure in the range of 10 to 600 atm. Another U.S. patent to Imai (U.S. Pat. No. 4,220,764 1980) teaches preparation of tertiary amines by a similar process except that the catalyst comprises a rhodium chloride rather than a rhodium carbonyl.

It is also known that phosphite ligands can be used to stabilize unsaturated rhodium species in order to hydroformylate otherwise unreactive olefins under mild conditions. No ruthenium carbonyl is employed in this process. See for example, Van Leeuwen et al report in an article in the J. Organometallic Chem. 258 (1983) 343–350.

In J. Org. Chem. 47, 445 (1991), Jachimowicz et al disclose various approaches which have been used in attempts to devise a one-step, efficient and general conversion of olefins to amines. Among the catalysts are iron pentacarbonyl, rhodium oxide, ruthenium/iron carbonyl and iridium catalysts.

In U.S. Pat. No. 4,297,481, Jachimowicz discloses a process for forming a polymeric polyamine/amide wherein said amino/amido nitrogens are positioned in the polymer backbone by contacting a monomeric nitrogen compound which has at least two labile hydrogens bonded to the nitrogen atoms therein, a monomeric hydrocarbon compound containing at least two olefinic groups therein, carbon monoxide and water in the presence of a catalytic amount of a rhodium-containing compound. This invention describes the use of ammonia or primary amines. The preparation of polymers with pendant amine and amide groups is also described in U.S. Pat. No. 4,312,965. These polymers are prepared from polymeric polyolefins, carbon monoxide, and monomeric nitrogen compounds as described previously. Again, rhodium or a rhodium-containing compound serves as the catalyst.

U.S. Pat. No. 4,503,217 teaches a process for preparing polymeric polyamines from polybutadiene, ammonia and primary or secondary amines in the presence of a catalyst system comprising a ruthenium-containing catalyst and a dimethyl formamide solvent which provides a two-phase liquid product, allowing for easy preparation of the product polyamine.

A review of prior art indicates that others have prepared similar materials such as polymeric polyamines. Specifically, poly(butadienes) having high vinyl content that comprise a high concentration of the 1,2-polybutadiene building block have been reacted with synthesis gas and secondary dialkylamines to provide dialkylaminemethylated polymers with a high degree of functionality. Others have formed similar materials but have been unable to functionalize the internal olefinic groups prevalent in lower cost polybutadiene that comprise in the main the 1,4-polybutadiene building block. Until recently, a good method has not generally been available for causing a reaction to occur in the internal olefin groups prevalent in lower cost polybutadiene. Very often these internal double bonds have remained in the final product or have been hydrogenated.

U.S. Pat. No. 4,657,984 discloses preparation of polymeric polyamines from CO, hydrogen, polymeric olefins and secondary amines utilizing as catalysts ruthenium or rhodium phosphines. It is stated that use of these particular catalysts facilitates reaction and hence functionalization of internal as well as vinyl olefin groups.

Thus, the state of the art for preparing polymeric secondary and tertiary polyamines teaches an aminomethylation reaction wherein the vinylic olefins and internal olefins can be reacted utilizing various catalysts under a variety of conditions. However, these reactions are significantly different than reductive amination reactions because there is no teaching in the prior art regarding aminomethylations on how to control the degree of functionalization, or the functional density, of either the polyaldehyde or of the polyamine prepared therefrom. For certain applications, it is desirable to control the functional density of the resulting polyamines. For example, it is desirable for certain applications, such as drug delivery, to further functionalize such polyamines utilizing residual unsaturation in the polymer material to link a drug to the polymer system. In addition, it is desirable, in certain circumstances, such as in drug delivery, to modify certain properties or characteristics of the polymer system, such as, for example, swelling characteristics by further functionalization such as by increasing the degree of cross-linking. Further functionalization of prior art polyamines utilizing remaining olefin groups is difficult, and in some cases is not possible because there is no appreciable degree of control over the reaction of such olefin groups in the process.

Accordingly, the present invention is directed to water insoluble controlled density polyamines which are cross-linked. These polyamines are particularly suitable for use in site specific delivery of drugs.

SUMMARY OF THE INVENTION

The present invention is directed to polymeric material containing a controlled multiplicity of amino nitrogen atoms and a controlled amount of unsaturation. A selected percentage of the amine groups are cross-linked. The present invention is also directed to a method of preparing such polyamines. The polyamines of the present invention are characterized in that they are water-insoluble and swell at pH values up to about 8 but do not swell at pH values above about 8. Because the functional density is controlled, such polyamines can contain residual unsaturation. The subject cross-linked polyamines can be further functionalized, such as by quaternization to render such polymers swellable at pH values above about 8 and by reacting additional functional groups with the residual unsaturated portion(s) of the polyamine such as by attaching a pH-sensitive linker material to which a drug can be attached or by attaching a drug directly thereto.

DETAILED DESCRIPTION OF THE INVENTION

The subject invention is directed to polyamines which are water-insoluble and swell up to pH values of about 8. These polyamines are prepared from a polymeric material having a multiplicity of olefinic groups therein. Such polymeric materials are reacted in the presence of a suitable hydroformylation catalyst system with carbon monoxide and hydrogen to form a controlled density polyaldehyde. The polyaldehyde is reductively aminated utilizing a monomeric amino compound and a hydrogen source, such as hydrogen, in the presence of a suitable reductive amination catalyst system to prepare a polyamine which is subsequently cross-linked. The resulting polyamine can be utilized in various applications such as, for example, drug delivery. Such polyamines can also be further functionalized such as, for example, by quaternizing the cross-linked polyamine. Alternatively, such polyamines can be quaternized and/or functionalized and then cross-linked.

A. Hydroformylation

The aldehyde-functionalized polymers are prepared taking advantage of unsaturation already existing in the polymer, i.e., beginning with an olefinic polymer. Such aldehyde-functionalized polymers preferably are prepared by a process comprising mixing an olefinic polymer with hydrogen and carbon monoxide in the presence of a Rhodium I catalyst. Preferably, the olefinic polymer has a weight average molecular weight (Mw) of at least 1000 and is selected from the group consisting of olefinic homopolymers and copolymers, and copolymers of olefins and at least one copolymerizable nonolefinic monomer.

The rhodium I catalysts suitable for use in the present invention are utilized at levels of less than 200 parts of catalyst based on metal rhodium per $10^6$ parts of polymer. Thus, the present process can be conducted economically, i.e., at low catalyst cost, and at relatively mild conditions.

In accordance with the present invention, the polyamines of the present invention are prepared, as stated above, from aldehyde-functionalized polymers which include both terminal and nonterminal aldehyde groups and taking advantage of unsaturation already existing in the polymer.

A preferred method for preparing the aldehyde-functionalized polymers useful in preparing the polyamine functional polymers of the present invention comprises mixing an olefinic polymer having a weight average molecular weight of at least about 1000 with less than 20 parts of a ligand-modified Rhodium I catalyst per $10^6$ parts polymer, and then reacting the resulting mixture with hydrogen and carbon monoxide at a temperature of from about 50°–150° C., preferably, 80°–130° C., such as at 100° C., and a total pressure of from 100 psig–2000 psig, preferably, 500–1500 psig, such as 1000 psig. Another method for preparing aldehyde-functionalized polymers which include terminal and nonterminal functional groups is disclosed in U.S. Pat. No. 3,383,426 and involves hydroformylating a polymer utilizing carbon monoxide and hydrogen in the presence of a phosphine or phosphite catalyst.

Olefinic polymers useful in the process of the present invention are those prepared from monomers represented by the formula $CH_2=CHR$ wherein R represents hydrogen and alkyl radicals having from 1 to about 12 carbon atoms which alkyl radicals may be unsaturated, e.g., where the monomer is a diene. Examples of such monomers include ethylene, propylene, 1-butene, 1-pentene, 1-hexene, 2-methyl-1-propene, 3-methyl-1-pentene, 4-methyl-1-pentene, 3,3-dimethyl-1-butene, 2,4,4-trimethyl-1-pentene, 3-methyl-1-hexene, 1,4-ethyl-1-hexene, 1,4-butadiene and the like.

Suitable polyolefins include homopolymers having residual double bonds therein such as polyethylene, polypropylene, polybutylene, polybutadiene, polyoctene; copolymers of olefins having residual double bonds therein such as poly(ethylene propylene), poly(ethylene octene), poly(ethylene isobutylene), poly(ethylene-1-butene), poly (ethylene-hexene), poly(propylene octene); copolymers of olefins having residual double bonds therein and at least one copolymerizable mono-olefinic monomer such as poly (ethylene propylene diene monomer), poly(ethylene vinyl acetate), poly(ethylene vinyl alcohol), poly(ethylene ethyl acrylate), poly(propylene methyl acrylate), copolymers of dienes and acrylonitrile such as a copolymer of butadiene and acrylonitrile; and the like.

Suitable polyolefins also include homopolymers of ethylene, propylene and butadiene; copolymers of ethylene and propylene; copolymers of ethylene and octene, e.g., linear low density polyethylene; copolymers of ethylene and vinyl acetate; copolymers of ethyl and vinyl alcohol which may also contain residual acetate groups; and copolymers of two or more olefins and a diene monomer such as poly (ethylene propylene diene monomer) EPDM. A preferred polyolefin is polybutadiene. Satisfactory diene monomers include straight chain (acyclic) dienes such as 1,4-hexadiene, 2-methyl-2,4-pentadiene, 1,4,9 decatriene and 11-ethyl-1,11-tridecadiene; monocyclic dienes such as 1,5-cyclooctadiene, dienes such as 5-ethylidenenorbornene (ENB), 5-methylene-2-norbornene; 5-isopropylidene-2-norbornene and 2-methyl-bicyclo-(2.2.1)-2,5-heptadiene; fused ring bicyclics such as bicyclo (4.3.0)-3,7-nonadiene; 5-methyl-bicyclo(4.3.0)-3-7-nonadiene; 5,6-dimethyl-bicyclo-(4.3.0)-3,7-nonadiene and bicyclo(3.2.0)-2,6-heptadiene; alkenyl substituted monocyclics such as 4-vinyl-cyclohexene; 1,2-divinylcyclobutane and 1,2,4-trivinylcyclohexane; and tricyclics such as dicyclopentadiene (DCPD). Grades of EPDM rubbers suitable for use in the practice of the invention are commercially available; Rubber World Blue Book 1975 Edition, *Materials and Compounding Ingredients for Rubber*, pages 406–410. Preferred EPDM rubbers are those marketed by Uniroyal Chemical Company, Inc., Middlebury, Conn. under the tradename Trilene®, such as Trilene® 66 and 67 (ENB diene monomers), Trilene® 55 and 65 (DCPD diene monomer) and the like. Other preferred EPDM rubbers include those wherein the diene monomer is 5-isopropylidene-2-norbornene. Although not specifically required, the ethylene to propylene ratio in such EPDM rubbers is preferably within a range of from about 40/60 to about 50/50.

In order to undergo the hydroformylation reaction the polyolefin used in the present invention must contain a level of unsaturation, i.e., as carbon to carbon double bond, which is the site where the syngas will form the aldehyde (—CHO) group. This unsaturation can be present in the backbone of the polymer and/or in a pendant group thereof, e.g., as in EPDM materials. Preferably the level of unsaturation in the polyolefin will be in the range of from one C=C per polymer chain (or molecule) up to about one C=C per 4 carbon atoms. Procedures for determining the level of unsaturation of polymers are well known. For example, the level of unsaturation can be determined utilizing ASTM D-1638-59T. The level of unsaturation can also be determined utilizing infrared spectroscopy or $^1$H nmr. This method can be conducted according to well-known procedures as described in Willard et al, *Instrumental Methods of Analysis*, Chapters 5 and 6, Van Nostrand Co., Inc., Publishers (1965). Alternatively, well-known titration methods can also be utilized. A preferred method for determining unsaturation levels is $^1$H nmr.

Suitable olefinic polymers have a weight average molecular weight (Mw) of from about 1000 to about 250,000. Preferred olefinic polymers are those having a Mw of from 600 to about 150,000, most preferably from 1,000 to about 15,000.

The olefinic polymer is mixed with carbon monoxide and hydrogen, with the polymer in the melt phase or dissolved in an inert solvent. Where no solvent is utilized, the polymer is heated to the Tg value corresponding to the specific polymer and then the carbon monoxide and hydrogen are added thereto and mixed. Where an inert solvent is utilized, the polymer is dissolved in the solvent and then the carbon monoxide and hydrogen are added and mixed. Suitable inert solvents for dissolving the polymer include toluene.

The hydrogen and carbon monoxide are mixed with the polymer in a $H_2/CO$ molar ratio of from about 1:3 to about 3:1, preferably from about 1:2 to about 2:1. A most preferred ratio is 1:1. Throughout the course of the reaction, the presence of $H_2$ and CO is preferably essentially maintained at the initial molar ratio.

Following addition of carbon monoxide and hydrogen, a suitable catalyst is added to the mixture. Alternatively, the catalyst can be mixed with the polymer prior to addition of the hydrogen and carbon monoxide. Suitable catalysts for hydroformylating the olefinic polymer include dicarbonyl acetylacetonate Rhodium I ($Rh(CO)_2AcAc$), cyclooctadiene trifluorgcetyl Rhodium I dimer ($[Rh(cod)(O_2CCF_3)])_2$, $RhH(CO)(PPh_3)_3$. A preferred catalyst is $RhH(CO)(PPh_3)_3$.

The components of the mixture are then reacted, at a temperature of from about 50° C. to about 225° C. and at a pressure greater than about 2.0 MPa, to produce the aldehyde-functionalized polymers. These polymers can have varying degrees of aldehyde functionalization and unsaturation depending on the amounts of carbon monoxide and hydrogen relative to the degree of unsaturation existing in the starting olefinic material.

In the following examples, the EPDM and polybutadiene polymers utilized were purchased. The rhodium hydroformylation catalysts were either purchased or prepared according to known literature procedures. Thus, $Rh(CO)_2$ (acetylacetonate) and $RhH(CO)(PPh_3)_3$ were purchased from Strem Chemicals, Inc., Newburyport, Mass. 01950. $[Rh(cod)(O_2CCF_3)]$ was synthesized according to the following procedure. $[Rh(1,5-cyclooctadiene)Cl]_2$ (made from $RhCL_3.3H_2O$ [Englehard Industries, Inc., Newark, N.J.] using the preparation described by G. Giordano and R. H. Crabtree found in *Inorg. Synth.*, Vol. 19, 218–220) (0.370 gm, 0.751 mmol) was placed in a Schlenk tube under Ar atmosphere and dissolved in 25 mL of degassed, dry toluene. $AgO_2CCF3$ (0.376 gm, 2.3 equiv.) was added to the bright yellow solution and allowed to stir for 2 hours. The solution was then filtered through diatomaceous earth to give a clear, bright yellow solution. The toluene solvent was then removed in vacuo. The yellow solids were then recrystallized by dissolving in 5 mL of $CH_2Cl_2$ and then adding 5 mL of hexanes. The $CH_2Cl_2$ was removed in vacuo and the remaining hexane solution was cooled to −78° C. in a dry ice/acetone bath to yield a fine yellow powder of the desired product. The bright yellow solid was isolated by filtration and dried in vacuo. The product was then recrystallized a second time by dissolving in $CH_2Cl_2$ and crystallizing from hexanes as before. The product was then characterized by $^1$H nmr and FTIR.

EXAMPLE 1

Solution Hydroformylation

In this method a 2-liter autoclave was charged with a specified amount of EPDM polymer (Nordel 1440 EPDM Hydrocarbon obtained from E. I. dupont de Nemours; diene monomer, 1,4-hexadiene; Mw of 290,000; Mooney viscosity of 40; 0.86 specific gravity; 55/39/6.2 Ethylene/Propylene/Diene Monomer weight percent) in solution in toluene and an effective amount of a soluble, ligand-modified metal complex catalyst. The autoclave was pressurized to 1500 psig with $CO/H_2$ and heated to 100° C. The reaction was continued while maintaining a flow of $CO/H_2$ to the system to maintain a $CO/H_2$ molar ratio of about 1:1 and maintain a constant autoclave pressure.

After specified periods of time, the reaction was stopped by venting off the gas and cooling the solution to 28° C. A representative portion of the reaction solution was removed and the polymer contained therein precipitated with methanol. The polymer was then analyzed by IR and $^1$H NMR for aldehyde functional groups. The runs were continued by again pressurizing the autoclave to 1500 psig with CO/H$_2$ and heating to 100° C. for additional intervals.

In Example 1, a 10 ppm level of dicarbonyl acetylacetonate Rhodium I was used to hydroformylate an EPDM polymer in solution.

The autoclave was charged with:

10 grams of EPDM polymer dissolved in 120 cc toluene, and, 0.1 mg of Rh(CO)$_2$AcAc and the solution processed in accordance with the procedure set forth above. The reaction was interrupted at 4.5, 12.0 and 20.0 hours and representative samples analyzed by IR and H$^1$ NMR. The results are tabulated in Table 1.

tion by slow addition of methanol (500 mL) with stirring. The solvents were then decanted and the polymer redissolved with 500 mL of toluene and precipitated again with 500 mL of methanol. After decanting the solvents, residual methanol was removed from the polymer by rotary evaporation leaving a light amber toluene solution of purified polyaldehyde. The extent of functionalization could be determined by comparing the integrals for the aldehyde groups and the residual olefin groups on the polymer in the $^1$H nmr.

EXAMPLE 3

EPDM-Polyaldehyde was produced using [Rh(cod)(O$_2$CCF$_3$)]$_2$(cod=1,5-cyclooctadiene) as the hydroformylation catalyst. The same procedure described in Example 1 was used except that [Rh(cod)(O$_2$CCF$_3$)]$_2$ was substituted for Rh(acac)CO)$_2$. When the same molar concentration of

TABLE 1

SUMMARY OF EXAMPLE 1

| Example | EPDM(G)/ 120 cc toluene | Weight (mg) Rh(CO)$_2$AcAc | Conc.* | Time (hrs) | Results IR | H$^1$ NMR |
|---|---|---|---|---|---|---|
| Control | 10 | 0 | 0 | 15.0 | IR shows no aldehyde peak. | H NMR showed no aldehyde. |
| (1) | 10 | 0.1 | 10 ppm | 4.5 | IR indicates aldehyde groups to be present. | H NMR indicates aldehyde groups to be present. |
| | | | | 12.0 | IR analysis indicates more aldehyde groups were produced. | |
| | | | | 20.0 | IR indicated aldehyde by the band at 1732. | H$^1$ NMR indicated aldehyde production. |

*Concentration of catalyst to polymer.

Example 1 demonstrates that successful solution hydroformylation of an EPDM polymer occurs at catalytic levels as low as 10 ppm.

EXAMPLE 2

A toluene solution of EPDM (Ethylene-Propylene-Diene Monomer) polymer was made by dissolving 300.05 gm of EPDM polymer (Trilene® 55 obtained from Uniroyal Chemical Co., Middlebury, Conn.; Ethylene/Propylene 48/52; diene monomer-dicyclopentadiene; Mn-6500, and Brookfield viscosity @100° C. of 67,000) in 500 mL of toluene and then degassing the solution by bubbling with argon. In a separate flask, Rh(acac)(CO)$_2$ (75.3 mg, 0292 mmol)(acac=acetylacetonate) was dissolved in 100 mL of toluene and the solution was degassed by bubbling with argon. Both solutions were placed in a 2 L reactor. The solutions were degassed with nitrogen three times in the reactor and then heated to 100° C. under 5 psig of nitrogen. The reactor was then charged to 1000 psig with 1:1 H$_2$/CO. The extent of reaction was measured by gas uptake from a calibrated reservoir. In this way the amount of aldehyde groups placed on the polymer backbone could be measured and controlled. At the desired functionality level, the reaction was stopped by quickly cooling the reactor and venting the H$_2$/CO gas from the reactor. The polymer solution was then removed from the reactor. The amount of toluene solvent was reduced by rotary evaporation and the hydroformylated polymer was precipitated from the toluene solucatalyst was used (based on Rh), [Rh(cod)(O$_2$CCF$_3$)]$_2$ was found to be just as effective a catalyst for hydroformylation as Rh(acac)(CO)$_2$.

EXAMPLES 4 TO 14

In Examples 4 to 14, hydroformylation of an EPDM polymer (Nordell 1440, described in Example 1) was performed according to the procedure set forth below under conditions which simulate the polymer in a melt phase. This procedure was performed utilizing dicarbonyl acetylacetonate Rhodium (I) and various levels of hydrocarbonyl tris (triphenyl phosphine) Rhodium (I).

Simulated Melt Phase Hydroformylation

In this method a stated amount of an EPDM (Nordell 1440) polymer and an effective amount of a specified catalyst were dissolved in toluene in a dry box. The solution was mixed well and the toluene removed by vacuum. A sample of the EPDM/catalyst was placed in a 30 cc Parr reactor in the dry box. The reactor was then heated to the stated temperature (150° C. to 215° C.) under a CO/H$_2$ pressure of 1000 psig. The reaction was continued while maintaining a flow of CO/H$_2$ to the system to maintain a CO/H$_2$ molar ratio of about 1:1 and a reactor pressure of about 1500 psig. Samples were removed at specified intervals and analyzed by IR and $^1$HNMR for aldehyde functional groups. The reaction conditions and results are set forth in Table 2.

TABLE 2

SUMMARY OF EXAMPLES 4 TO 14

| EXAMPLE | EPDM(g) | Catalyst/wt(g) | | Conc.* | Temp. (°C.) | $CO/H_2$ (psig) | Time (min.) | | |
|---|---|---|---|---|---|---|---|---|---|
| (4) | 0.10 | — | 0.00 | 0 | 150. | 1000. | 150. | IR shows no aldehyde peak. | |
| (5) | 1.00 | — | 0.00 | 0 | 150. | 1000. | 4275 | IR shows trace peak at 1738. | H NMR after 11709 transients showed no aldehyde. Olefin had isomerized. |
| (6) | 0.10 | A | 0.01 | 10 pph | 150. | 1000. | 150. | IR shows aldehyde peak at 1726 and acid peak at 1707. | |
| (7) | 0.10 | A | 0.01 | 10 pph | 150. | 1000. | 315. | IR shows aldehyde peak at 1730. | |
| (8) | 0.10 | A | 0.01 | 10 pph | 215. | 1000. | 125. | IR shows aldehyde peak at 1730. | |
| (9) | 0.10 | B | 0.01 | 10 pph | 150. | 1000. | 360. | IR shows aldehyde peak at 1730 also a peak at 1794 due to the catalyst. | |
| (10) | 1.00 | A | 0.01 | 1 pph | 150. | 1000. | 1110. | IR shows aldehyde peak at 1730. | H NMR shows no olefin. |
| (11) | 1.00 | A | 0.001 | 0.1 pph | 150. | 1000. | 1050. | IR shows aldehyde peak at 1732. | H NMR shows approx. 50% olefin. |
| (12) | 1.00 | A | 0.0001 | 100 ppm | 175. | 1000. | 1140. | IR shows aldehyde peak at 1732. | H NMR shows olefin and trace aldehyde. |
| (13) | 1.00 | A | 0.00001 | 10 ppm | 200. | 1000. | 1080. | IR shows trace aldehyde peak at 1732. | H NMR after 11294 transients showed trace <90% olefin. |
| (14) | 1.00 | A | 0.0001 | 1 ppm | 200. | 1000. | 4115. | IR shows trace peak at 1740. | H NMR after 11004 transients showed no aldehyde. Olefin has isomerized. |

Catalyst A: hydrocarbonyl tris(triphenyl phosphine) Rhodium (I)
Catalyst B: dicarbonylacetyl acetonate Rhodium (I)
*Concentration of catalyst to polymer.

Examples 4 and 5 demonstrate that the presence of a catalyst is needed to initiate the hydroformylation reaction. Increased temperatures and extended reaction times do not result in the production of aldehyde-functionalized EPDM polymers in the absence of an appropriate catalyst.

Examples 6 through 8 show the successful hydroformylation of EPDM utilizing a 10 pph level of hydrocarbonyl tris(triphenyl phosphine) Rhodium (I). Higher temperatures result in lower reaction times.

Example 9 demonstrates the successful hydroformylation of EPDM utilizing a 10 pph level of dicarbonyl acetylacetonate Rhodium (I).

Examples 10 through 14 show the hydroformylation of EPDM utilizing levels of catalyst as low as 10 ppm. Example 13, in particular, demonstrates the hydroformylation of EPDM containing 10 ppm of hydrocarbonyl tris (triphenyl phosphine) Rhodium I at 200° C. and 1000 psig ($CO/H_2$ 1:1) in the absence of solvent.

EXAMPLE 15

A toluene solution of polybutadiene polymer (Aldrich Chemicals cat. no. 20050–6; Mn 4500, 45% vinyl, 55% cis and trans-1,4) was made by dissolving 350.70 gm of polybutadiene in 600 mL of toluene and then degassing the solution by bubbling with argon. In a separate flask, $Rh(acac)(CO)_2$ (27.0 mg, 0.105 mmol) (acac= acetylacetonate) was dissolved in 100 mL of toluene and the solution was degassed by bubbling with argon. Both solutions were placed in a 2 L reactor the solutions were degassed with nitrogen three times in the reactor and then heated to 100° C. under 5 psig of nitrogen. The reactor was then charged to 1000 psig with 1:1 $H_2/CO$. The extent of reaction was measured by gas uptake from a calibrated reservoir. In this way the amount of aldehyde groups placed on the polymer backbone could be measured and controlled. At the desired functionality level, the reaction was stopped by quickly cooling the reactor and venting the $H_2/CO$ gas from the reactor. The polymer solution was then removed from the reactor. The amount of toluene solvent was reduced by rotary evaporation and the hydroformylated polymer was precipitated from the toluene solution by slow addition of methanol (500 mL) with stirring. The solvents were then decanted and the polymer redissolved with 500 mL of toluene and precipitated again with 500 mL of methanol.

After decanting the solvents, residual methanol was removed from the polymer by rotary evaporation leaving a light amber toluene solution of purified polyaldehyde. The extent of functionalization could be determined by comparing the integrals for the aldehyde groups and the residual olefin groups on the polymer in the $^1$H NMR.

EXAMPLE 16

Under a stream of nitrogen, a 2.0 liter autoclave is charged with 289.0 grams of polybutadiene, 308 ml of toluene, 12.7 g triphenylphosphine, and 0.27 of hydrocarbonyl tristriphenyl-phosphine rhodium. The reaction was heated to 80° C. under nitrogen and then charged with 300 psig of $CO/H_2$ and stirred at 1000 rpm's until the 33.5% of the butadiene units were hydroformylated. The reaction is done in approximately 3.5 hours. The proton NMR confirms the extent of reaction. The reaction mixture is removed from the clave and toluene is used to aid in the transfer. The solution is filtered to remove particulates and concentrated to 500 g. A 250 gram portion of this solution was slowly dripped into 1000 cc of methanol/water (80/20 v/v) with stirring. After stirring for an additional 15 minutes, stop stirring and let set for 1 hour. The bottom polymer layer is isolated and the washing step is repeated. Redissolve the dry polymer in toluene and store in the dark.

EXAMPLE 17

Production of EPDM Polyaldehyde - A toluene solution of EPDM (Ethylene-Propylene-Diene Monomer) polymer was made by dissolving 300.05 gm of EPDM polymer in 500 mL of toluene and then degassing the solution by bubbling with argon. In a separate flask, $Rh(acac)(CO)_2/CO$ (75.3 mg, 0.292 mmol) (acac=acetylacetonate) was dissolved in 100 mL of toluene and the solution was degassed by bubbling with argon. Both solutions were placed in a 2 L reactor. The solutions were degassed With nitrogen three times in the reactor and then heated to 100° under 5 psig of nitrogen. The reactor was then charged to 1000 psig with 1:1 $H_2/CO$. The extent of reaction was measured by gas uptake from a calibrated reservoir. In this way the amount of aldehyde groups placed on the polymer backbone could be measured and controlled. At the desired functionality level, the reaction was stopped by quickly cooling the reactor and venting the $H_2/CO$ gas from the reactor. The polymer solution was then removed from the reactor. The amount of toluene solvent was reduced by rotary evaporation and the hydroformylated polymer was precipitated from the toluene solution by slow addition of methanol (500 mL) with stirring. The solvents were then decanted and the polymer redissolved with 500 mL of toluene and precipitated again with 500 mL of methanol. After decanting the solvents, residual methanol was removed from the polymer by rotary evaporation leaving a light amber toluene solution of purified polyaldehyde. The extent of functionalization could be determined by comparing the integrals for the aldehyde groups and the residual olefin groups on the polymer in the $^1$H nmr.

EXAMPLE 18

Production of poly(butadiene) Polyaldehyde - A toluene solution of polybutadiene polymer (Aldrich Chemicals cat. no. 20050–6;aver. M. N. 4500, 45% vinyl, 55% cis and trans-1,4) was made by dissolving 350.70 gm of polybutadiene in 600 mL of toluene and then degassing the solution by bubbling with argon. In a separate flask, $Rh(acac)(CO)_2$ (27.0 mg, 0.105 mmol)(acac=acetylacetonate) was dissolved in 100 mL of toluene and the solution was degassed by bubbling with argon. Both solutions were placed in a 2 l reactor. The solutions were degassed with nitrogen three times in the reactor and then heated to 100° C. under 5 psig of nitrogen. The reactor was then charged to 1000 psig with 1:1$H_2$/CO. The extent of reaction was measured by gas uptake from a calibrated reservoir. In this way the amount of aldehyde groups placed on the polymer backbone could be measured and controlled. At the desired functionality level, the reaction was stopped by quickly cooling the reactor and venting the $H_2$/CO gas from the reactor. The polymer solution was then removed from the reactor. The amount of toluene solvent was reduced by rotary evaporation and the hydroformylated polymer was precipitated from the toluene solution by slow addition of methanol (500 mL) with stirring. The solvents were then decanted and the polymer redissolved with 500 mL of toluene and precipitated again with 500 mL of methanol. After decanting the solvents, residual methanol was removed from the polymer by rotary evaporation leaving a light amber toluene solution of purified polyaldehyde. The extent of functionalization could be determined by comparing the integrals for the aldehyde groups and the residual olefin groups on the polymer in the $^1$H nmr. This reaction has also been performed with RhH $(CO)(PPh_3)_3$ as the catalyst.

B. Reductive Amination

Reductive amination is conducted by reacting the above-described polyaldehyde with an amine and a hydrogen source in a suitable solvent, and in the presence of a suitable catalyst system. See, for example, Marko et al, *J. Organometallic Chem.*, 81, 411 (1974).

Suitable amines include secondary amines, examples of which include, but are not limited to, straight and branched chain aliphatic secondary amines, cycloaliphatic secondary amines and aromatic secondary amines. Specific examples of such amines include dimethylamine, diethylamine, methylethylamine, n-methylethanolamine, di(n-propyl) amine, di(iso-propyl)amine, di(ethylhexyl)amine, piperidine, morpholine, piperazine, di)n-heptyl)amine, di(n-docyl)amine, n-methylaniline, pyrrolidone, 2-aminooctane and the like, including mixtures thereof. Polyamines such as hexamethylene diamine, tetraethylene-pentamine and the like are also suitable.

The ratio of amine to polyaldehyde will vary depending on the aldehyde functional density of the polyaldehyde and the desired amine functional density of the resulting polyamine. Such ratio can vary from about 1:1 to about 30:1 (as molar ratios), such as from about 1:1 to about 20:1, preferably from about 1:1 to about 10:1. The resulting polyamines can contain functional groups wherein all or most of the aldehyde groups are aminated, or wherein only a desired percentage of the aldehyde groups are aminated.

The amine functional density will depend on the aldehyde functional density. Thus, the amine functional density can range from about 10% to about 80%, such as from about 25% to about 75%, preferably from about 30% to about 50%, depending on the molecular weight of the polymer, the degree of cross-linking and the desired swelling characteristics.

Suitable catalyst systems include ruthenium carbonyl as well as acetoxy borohydride and sodium cyanoborohydride. Where the catalyst system utilized is one such as the ruthenium carbonyl catalysts, an external source of hydrogen, e.g., $H_2$, will be required. See, for example, Hayashi et al., *J. Mol. Cat.*, 58, 165 (1990).

The resulting polyamines can be cross-linked prior to functionalization by methods which are well known in the art. The cross-linking agent selected to be incorporated in the delivery system herein can be any suitable cross-linking agent which can cross-link the polymer selected for use in the system. The selection of a cross-linking agent is within the level of skill in the polymer art. Depending upon the polymer selected, the cross-linking agent can be a dialdehyde, diacid, disilane, dihaloxylene, tri(halomethyl)benzene, dihaloalkane, dihaloalkene, diallylhalide, or any polyaromatic, aliphatic or allylic halide, and the like. For example, such polyamines can be reacted with a cross-linking agent such as 1,3,5-tris(chloromethyl)benzene, α,α'-dichloro-p-xylene, 1,6-dibromohexane in a suitable solvent and for a period of time depending on the amount of cross-linking agent and the desired degree of cross-linking. Alternatively, the polyamines can be further functionalized and then cross-linked.

The degree of crosslinking can vary depending on the amine functional density, the molecular weight of the starting olefin polymer, and the desired characteristics of the resulting water-insoluble polyamine. See FIG. 2, for example. For example, the degree of crosslinking can vary from about 5% to about 100% based on the amine functional density, such as from about 5% to about 50%.

Figure 1:
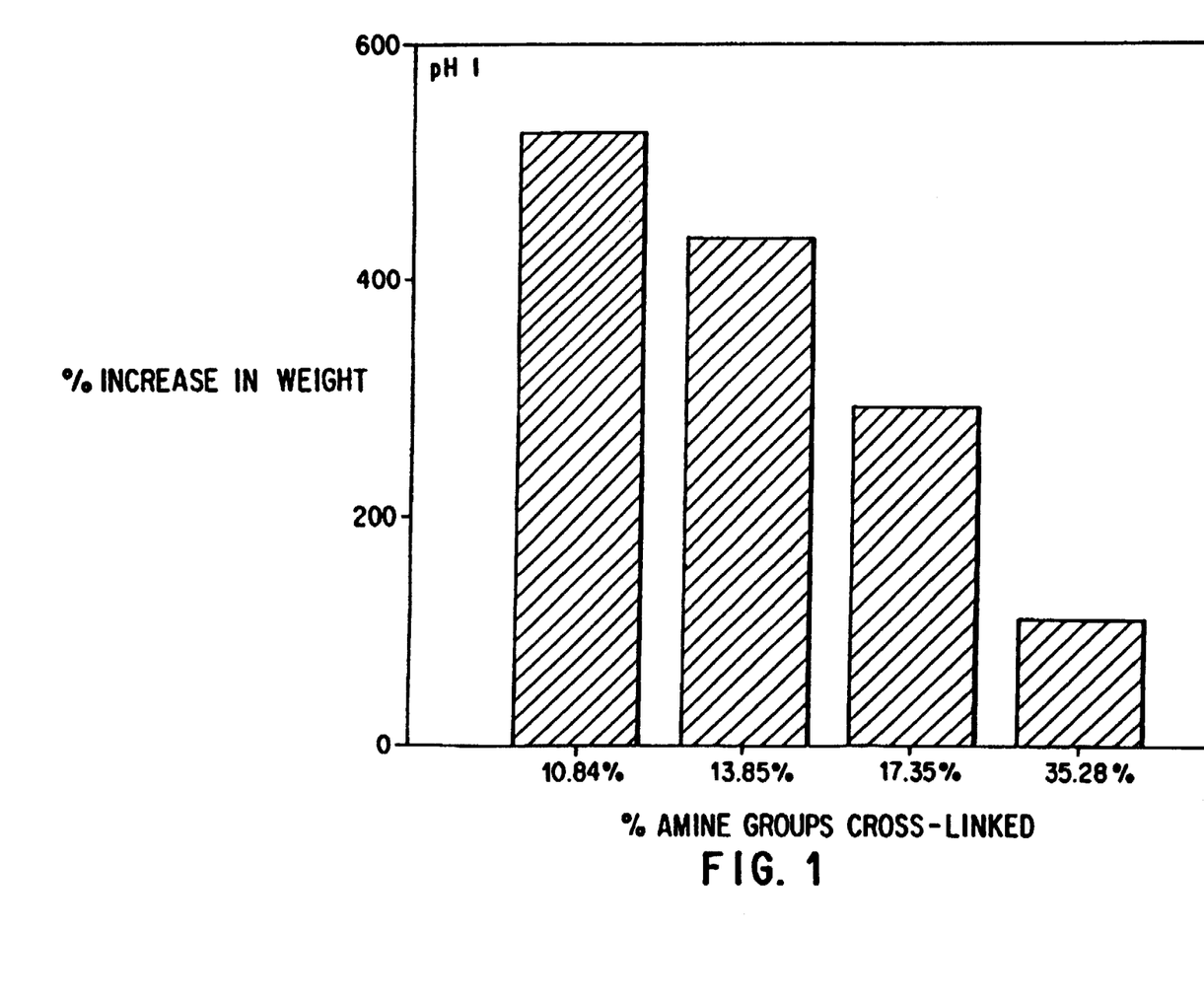
FIGS. 1–3 are bar graphs illustrating the swelling characteristics of the polyamines of the present invention at various degrees of cross-linking (FIG. 1), amine concentration (FIG. 2), and pH values (FIG. 3).
Figure 2:
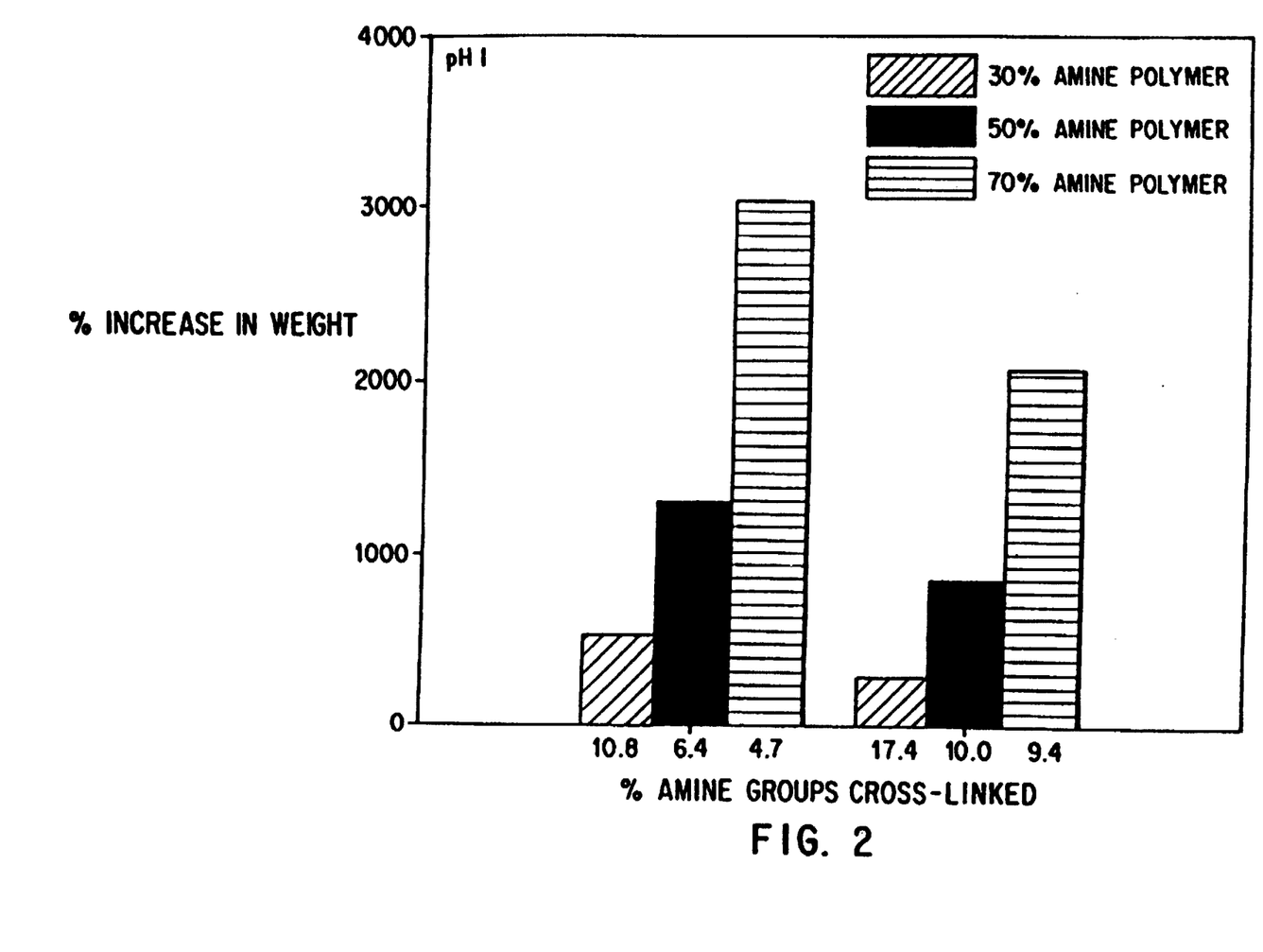
Figure 3:
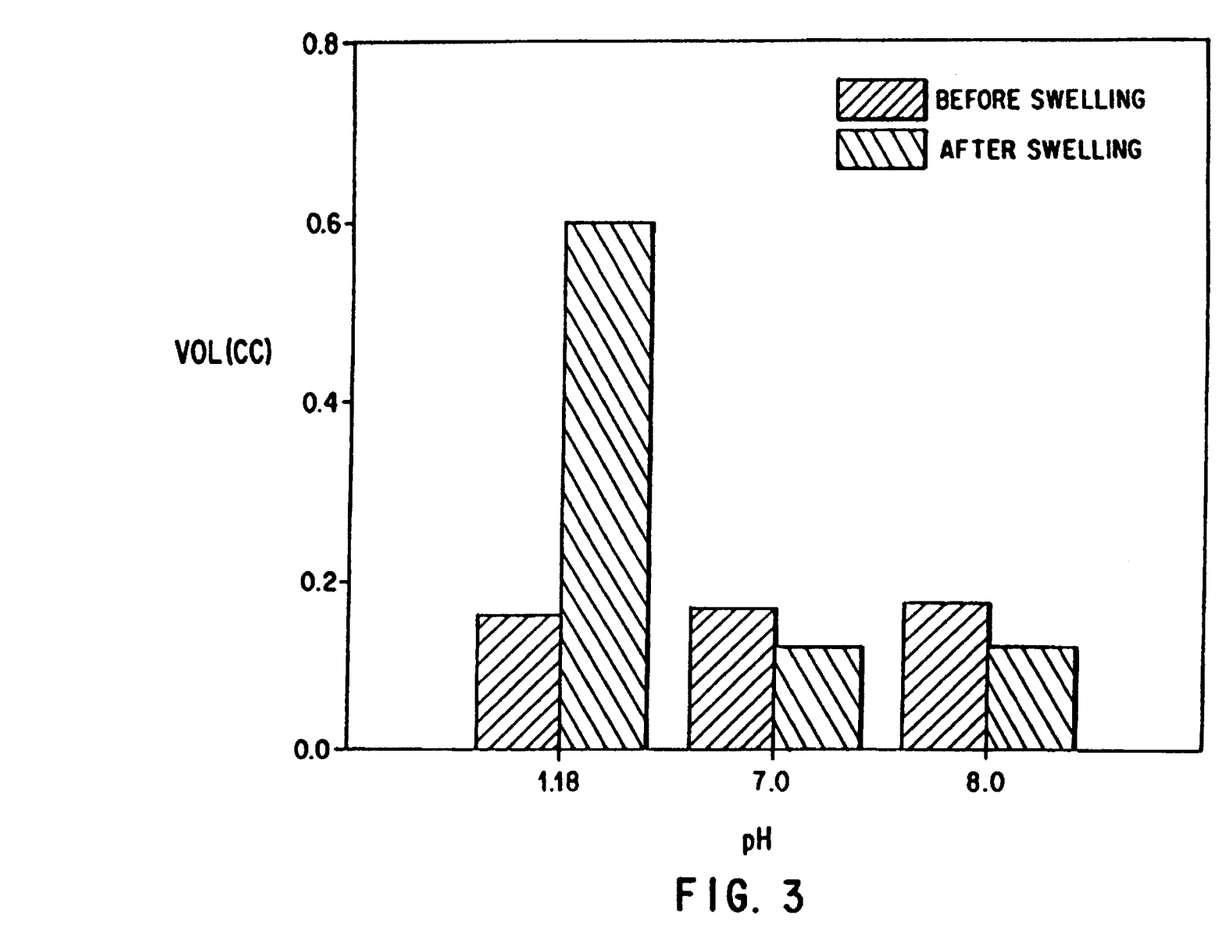

The polyamines of the present invention can be cross-linked to varying degrees depending on the desired swelling characteristics. FIG. 1 illustrates the degree of swelling of polyamines of the present invention as a function of cross-linking. FIG. 2 illustrates the degree of swelling of polyamines of the present invention as a function of amine concentration (functional density of amine). FIG. 3 illustrates the degree of swelling of polyamines of this invention at various pH values.

Thus, the controlled density polyamines of the present invention are prepared in two steps so that the functional density of the polyaldehyde, and the functional density of the polyamine produced therefrom are both controlled.

EXAMPLE 19

This example illustrates the preparation of a polyamine according to the teachings of the present invention. Toluene was removed from the polyaldehyde prepared in Example 16 by means of a vacuum. The polyaldehyde (300.20 g) was then diluted with 785 ml of DMF and the samples were divided into two separate batches. The reductive amination was done in two batches. A 2 liter autoclave (clave) was charged with 150 grams of polyaldehyde in 392.5 mL DMF, 330 mL cyclohexane, 112 g dimethylamine and 1.5 g ruthenium carbonyl. The clave was sealed and then quickly purged with 100 psig CO/$H_2$. The clave was then charged with 100 psig of CO/$H_2$ and 900 psig of $H_2$ and heated to 120° C. at 1000 rpm's. The extent of reaction was determined by gas uptake and the reaction was completed in approximately 2 hours. After cooling to room temperature, the contents of the clave were removed and placed in a 1 liter separatory funnel and allowed to phase out. The lower reddish-brown DMF level was removed and discarded. 300 cc of DMF were added to the separatory funnel and cyclohexane added to the original volume. This extract procedure was repeated for a total of three times. Next the cyclohexane layer was filtered with a medium porosity glass-fritted Buchner funnel. Residual DMF was removed through azeotropic distillation at 50° C. using toluene.

EXAMPLE 20

This example illustrates one method of cross-linking the polyamines according to the teachings of the present invention.

1) Cross-linked polyamine - In a 250 ml round-bottom flask weigh out 12 gms of polyamine (Example 1) and prepare a 30 wt. % solution of polyamine in THF. With stirring, add 0.945 gms of α,α' dichloro-p-xylene in 2.25 gm THF. Wash in with 1 c more THF. Allow to stir until set. Let set for 60 hours at room temperature. Next, cut cross-linked polymer with a spatula and grind in an analytical mill. Transfer the white solid to a 2-liter beaker and stir with 1 liter THF for 1 hour. Filter using a 600 ml coarse filter funnel. Repeat cleanup for a total of five times. Elemental analysis of dry material: % C 77.41; % H 11.55; % N 5.71, % Cl 3.42.

2) Methylated Polyamine - The cross-linked polyamine from Step 1 is placed in a 12 oz. Fischer-Porter bottle and THF is added to obtain a total volume of 210 mls (premeasured). cap and cool to −78° C. for ½ hour. Next bubble in methylchloride until the volume increases by 20% (252 cc premeasured). Seal and warmup to room temperature by removing the −78° C. bath. Stir for 60 hours and then vent and remove the unreacted methyl chloride by purging with nitrogen gas. Filter the white solid using a coarse glass frit funnel. Wash methylated cross-lined polymer with 1 l THF. Elemental analysis of dry sample: % C 68.53, % H 10.66, % N 4.85, % Cl 11.99.

C. Further Functionalization

The cross-linked polyamines of the present invention can be further functionalized. For example, such polyamines can be functionalized by attaching a pH-sensitive drug linker, e.g., a chlorodimethylsilyl linker, directly to the polymer utilizing residual unsaturation existing in the polymer backbone. In addition, the amino groups can be quaternized to further functionalize the polyamines. For example, such cross-linked polyamines can be quaternized to an extent such that they swell at pH values above about 8. Alkyl halides suitable for quaternization include methyl chloride, ethyl chloride, benzyl chloride and the like. Other means for functionalizing such polyamines will be obvious to those skilled in the art in view of the teachings of the present invention. For example, certain of the polymers that can be used herein can also be modified by attaching auxiliary groups which can impart certain properties such as gastric retention, hydrophilicity, crystallinity and the like. For example, auxiliary groups such as dialkylamino groups or quaternized ammonium salts can be employed to control certain properties, such as hydrophilicity, swelling, crystallinity and the like to effect the drug release rate. It should be noted that the polyamines of the present invention can be functionalized and then cross-linked, or cross-linked, and then functionalized, or partially cross-linked, then functionalized and then further cross-linked, depending on the degree of further functionalization and the degree of cross-linking desired.

EXAMPLE 21

This example illustrates one way of producing further functionalized polyamines according to the teachings of the present invention.

A 75 g sample of Polybutadiene (Aldrich 20,050–6 45% vinyl $M_w$=4500) was dissolved in 75 ml of toluene. Under a $N_2$ atmosphere, this polymer solution was pored into a 300 ml autoclave. Next 3.3 g triphenylphosphine and 0.07 g of hydridorhodiumcarbonyltristripphenyl- phosphine were added to the clave under $N_2$. The clave was sealed and further degassed with $N_2$ by pressurizing the clave with 200 psi $N_2$ and then venting off the $N_2$ gas. The clave was heated to 80° C. under 400 psi $N_2$. After removing the $N_2$, the clave was charged with 300 psi 1:1 CO/$H_2$ at 80° C. The reaction was stirred at 1200 rpm until 0.917 moles of 1:1 CO/$H_2$ were reacted. After venting the clave, the polymer product was removed. The clave was washed with 100 ml of toluene and the washings were added to the polymer product. the product solution was concentrated to a 150 ml volume by means of a rotary evaporator. This polymer solution was slowly dripped into a solution containing 400 ml methanol and 100 ml water. The solution was allowed to separated into two phases and the top phase was removed by decantation. The bottom polymer phase was dissolved in 150 ml toluene and the above precipitation procedure was repeated. From this procedure 63.64 g of polymer product was isolated. $^1$H NMR indicated that 32% of the double bonds in the polybutadiene polymer [P(bd)] were hydroformylated.

A solution of the formyl-functionalized polymer (63.14 g) in 100 ml of sieved dried toluene and 20 ml methanol was placed in a two-liter, 3-neck round bottom flask equipped with a thermometer, addition funnel and a magnetic stir bar. The solution was further diluted with 500 ml of tetrahydrofuran and 40 ml of methanol. After cooling to 5° C. under nitrogen, 50 g of dimethylamine was added with stirring. After 15 minutes and by means of an addition funnel, 85.8 ml of a 4.5M HCl/dioxane solution was slowly added to the solution. Finally, 17 g of sodium cyanoborohydride (sodium triacetoxy borohydride can also be used but does not require the use of the HCl/dioxane addition) was added by means of a funnel and rinsed into the flask with 20 ml of tetrahydrofuran. The solution was stirred for 40 hours and allowed to warm slowly to room temperature. The polymer solution was filtered after it was stirred with 60 ml of water for one hour. The filtrate was concentrated to a 200 ml volume and after settling for two hours, the top polymer phase was slowly dripped into a solution containing 400 ml methanol and 100 ml water. The bottom polymer phase was isolated by decantation. This precipitation procedure was repeated. From this procedure 64.6 g of polyamine was isolated. % C, 80.62; %H, 11.66; %N, 6.62.

An 84.5 g sample of a 29.6 wt. % solution of the above polyamine (25 g of polyamine) in toluene was added to a Fischer-Porter bottle that was equipped with a stir bar. The solution was concentrated to 50 g by means of a vacuum and the evacuated vessel was brought into the dry box. Dry toluene was added in order to prepare a 50 wt.% solution. Next 0.125 g tristriphenylphosphine rhodium chloride and 12.5 g chlorodimethylsilane were added to this solution. After capping and removing the reactor from the dry box, the solution was heated to 100° C. for 17 hours. The solution was transferred to a dry 250 ml round bottom flask in a dry box. The solution was concentrated to 37.6 g (to remove unreacted silane) and diluted with 100 ml dry tetrahydrofuran. $^1$HNMR indicated 2.0% chlorosilane incorporation.

The above chlorosilylated polyamine in THF was diluted with 100 ml of DMF (dried over alumina). After 1 hour 0.090 g imidazole (1.3 mmoles) in 5 ml of THF was added slowly and dropwise (other amines an also be present such as triethylamine). After 15 minutes 0.5 g of misoprostol (1.3 mmoles) in 5 ml THF was added and rinsed into the solution with 2 ml THF. After stirring for 6 hours, 0.583 g imidazole (8.56 mmole) in 15 ml THF was added dropwise with stirring. Next 0.411 g methanol in 2 ml THF was added and allowed to stir for 16 hours. After adding an additional one ml of methanol, the product solution was evaporated to remove all of the THF. The remaining DMF/polymer solution was allowed to stand for 1 hour in order to phase separate the polymer from the DMF solvent. The top polymer layer was separated and further dried by vacuum to remove trace DMF. From this procedure 20.6 g of polymer product was isolated.

The above polymer in THF (27.5 wt. % solution) was stirred in a 250 ml round bottom flask. Next 1.497 g (8.55 mmoles) of α,α'-dichloro-p-xylene in 10 g THF was added dropwise to the stirred polymer solution. The product set up in 4 hours and was allowed to stand at room temperature for 20 hours. The solid product was removed with a spatula and divided into three equal parts. Each portion was washed by the following procedure by use of a wrist shaker:

a) Shaken With 200 ml THF for 0.5 hrs. and filtered and the collected solid was washed in the same manner.

b) THF was removed from the filtered polymer by vacuum.

c) The polymer was washed twice with nanopure water as in procedure a).

d) Repeated a) twice.

e) The collected portions were combined and dried for 4 hours under vacuum.

From this procedure 17.5 g of cross-linked polyamine were isolated. Elemental analysis: %C, 77.3; %H, 11.4; N, 5.65; %Cl, 3.51.

The product was evaluated for swelling. The product was found to swell at a pH of about 1 to 7. Reaction of a 25 mg sample of this material with 3 ml methanol and 3 ml pH 1 acid resulted in release of the misoprostol by HPLC.

EXAMPLE 22

This example illustrates a drug delivery system having misoprostol incorporated in the cross-linked polyamine system of Example 21 is further functionalized by quaternization.

An 8 g sample of the cross-linked polyamine from Example 21 and 160 ml of dry THF were stirred in a 16 oz. Fisher Porter bottle for 4 hours. Next 9 ml of dry methyl chloride was added at −78° C. After stirring for 64 hours and after removing the methyl chloride by degassing, the polymer product was filtered. After drying by vacuum, 9.7 g of methylated product was isolated. % C, 68.11; %H, 10.60; %n, 4.99; %Cl, 11.01. A 9.53 g sample of the cross-linked polymer was milled at liquid nitrogen temperature for 5 minutes to obtain 9.33 g of a fine powder. The milled material was placed in a mortar and 9.33 g of hydroxypropylmethylcellulose were added and mixed well with a pestle. This material was transferred to the mill at room temperature and ground for 3 minutes. This formulation was ball milled for 9 hours and sieved with a 250 micron sieve. From this procedure 17.4 g of polymer product (<250 micron) was recovered.

The methylated (quaternized) product was evaluated for swelling. The methylated product was found to swell within the pH range of about 1 to 8. Reaction of a 50 mg sample of this material with 3 ml methanol and 3 ml pH 1 acid resulted in release of the misoprostol as determined by HPLC. Reaction of a 50 mg sample of this material with 3 ml methanol and 3 ml water at pH 7 resulted in no detectable release of the misoprostol after 1 hour as determined by HPLC.

EXAMPLE 23

Ten grams of the polyamine (34.88 g polyamine/toluene solution) of Example 19 were placed in a 6 oz. Fischer porter bottle. After capping, most of the toluene and air were removed by vacuum distillation with stirring. The reactor was placed into a dry box and 0.1 g chlorotriphenylphosphine rhodium and 9.58 g toluene were added to bring the solution to 50 wt %. Then 0.741 grams of isopropylethylchlorosilane were added. The reactor was capped and heated at 100° C. by means of a temperature controlled oil bath for 17 hours. The reaction container was transferred to a dry box and the reaction solution was then transferred to a dry 250 mL R. B. flask with stir bar. The reactor was washed with dry THF and a total of 50 g THF was added to the reaction product. Next, 50 mL of dry DMF was added. The mixture was stirred for 0.5 hrs. The THF was removed through vacuum distillation. The toluene and the polymer separated from the remaining DMF solution. The polymer was poured into a 125 mL separatory funnel and allowed to phase out for 1 hour. The lower DMF layer and the polymer were redissolved with 50 grams of dry THF. Forty grams of DMF were added and the separation procedure was repeated. The polymer was redissolved in 100 mL of dry cyclohexane and extracted with 80 mL of DMF. 20 mL of cyclohexane were added to the cyclohexane phase and again extracted with 80 mL of DMF. The polymer was stored in dry THF.

EXAMPLE 24

This example illustrates further functionalization of the polyamines of the present invention utilizing a chloromethylphenylsilyl linker to which a drug, namely misoprostol, is attached. This example also illustrates further functionalization by quaternizing and cross-linking after functionalization.

A 34.88 gm aliquot of polyamine solution (10 gms of polyamine in toluene) was added to a Fischer-Porter bottle that was equipped with a stir bar. The solution was concentrated and adjusted to 50 wgt % in toluene. After transferring to a dry box, 0.1 gms of chloro tristriphenylphosphine rhodium chloride was added to the polyamine solution and stirred for five minutes. Next 0.852 gms of phenylmethylchlorosilane was added. After capping and removing the reactor from the dry box, the solution was heated at 100° C. for 17 hours. In a dry box reaction solution was transferred to a 250 ml r.b. flask and diluted to 50 gms with THF. After adding 25 gms DMF and stirring for 0.5 hours, the THF and toluene was removed by vacuum, the polymer mixture was transferred to a separatory funnel. After phase separation, the bottom DMF phase was removed. Using THF, the polymer was dissolved in 50 gm THF and stirred with 40 gms DMF for 0.5 hours. Again, the THF was removed by vacuum and polymer phase was separated. The resulting chlorophenylmethylsilylated polymer (9.83 gms) was diluted with 34.95 gms of THF and 37.06 gms of DMF. Next 0.109 gms triethylamine (0.514 mmole), 0.35 gms of imidazole (0.514 mmols) and 0.197 gms of misoprostol were added (0.514 mmoles) and this solution was stirred for 17 hours. After 17 hours, 0.198 gms triethylamine, 0.2 gms imidazole and 0.417 gms methanol were added and stirred for 1 hour. The product solution was then evaporated to remove all of the THF and allowed to stand for 1 hour to phase separate the polymer from the DMF solution. The product was then cross-linked and methylated following the procedures of Examples 21 and 22.

Elemental Analysis

| After cross-linking | % C 75.48; % H 10.52; |
|---|---|
|  | % N, 5.41; % Cl 3.49 |
| After methylation | % C, 68.60; % H 10.89; |
|  | % N, 4.46; % Cl 11.45 |

Reaction of a 50 mg sample of the methylated material with 3 ml methanol and 3 ml pH 1 acid resulted in release of misoprostol by HPLC (80% release after 1 hour). Reaction of a 50 mg sample with 3 ml methanol and 3 ml pH 4 acid resulted in 1% release of misoprostol after 2 hours.

EXAMPLES 25–28

For the following examples 25 through 28, the procedure from Example 24 was followed except that other pH-sensitive drug linkers were substituted for the chlorosilane utilized in Example 24. The resulting systems were then analyzed and tested to determine release of drug at different pH values. Results are shown in Table 3.

TABLE 3

| | | CROSS-LINKED | | | | METHYLATED | | | | % released in 1 hr pH1 | % Released in 1 hr at pH 6–7 |
|---|---|---|---|---|---|---|---|---|---|---|---|
| Example | Silane (gms) | % C | % H | % N | % Cl | % C | % H | % N | % Cl | Misoprostol | Misoprostol |
| 25 | Ph$_2$SiHCl (1.19 g) | 75.91 | 10.90 | 5.17 | 3.60 | 69.41 | 10.42 | 4.14 | 11.72 | 62% | Trace to small to quantify pH 7. |
| 26 | PhSiEtHCl | 76.96 | 11.57 | 5.31 | 3.90 | 69.09 | 11.33 | 4.71 | 10.99 | Releases at pH1 | — |
| 27 | Diisopropylchlorosilane (0.82 g) | 76.6 | 11.78 | 5.42 | 3.73 | 69.09 | 11.32 | 4.71 | 10.99 | ~5% | — |
| 28 | Et$_2$SiHCl (2.58) | 75.1 | 11.43 | 5.08 | 3.65 | 57.0 | 9.41 | 3.70 | 9.37 | 83% | Nondetected by HPLC (pH6) |

*50 mg sample in 3 cc acid and 3 cc methanol.

EXAMPLE 29

This example illustrates utilization of another cross-linking material. The misoprostol-bound polyamine was prepared according to the procedure set forth in Example 21. Three grams of this polymer was diluted with THF to obtain 10.12 g of a THF solution. Next 0.311 g of 1,3,5-tris(chloromethyl)benzene in 1 cc THF was added to this solution and washed in with 0.5 g more THF. This solution was then allowed to set for 54 hours. The cross-linked polymer was ground in an analytical mill at room temperature for 5 minutes, transferred to a 2-liter beaker and stirred with 1 liter of THF for 1 hour. The polymer was allowed to settle and then filtered with a glass frit buchner funnel. This cleanup step was repeated for a total of 5 washes, after which 3.1 gms of cross-linked polymer was isolated. Elemental analysis: %C, 73.91; %H, 11.0; %N, 4.65; %Cl 4.93.

The cross-linked polyamine was methylated as in Example 21. Elemental Analysis %C, 65.93; %H, 11.04; %N, 4.14; %Cl, 11.15.

|  | (Vol.)<br>Wt. before swelling | (Vol.)<br>Wt. after swelling |
|---|---|---|
| Swelling Studies: |  |  |
| pH 7 | 50.3 mg (5 mm) | 242.6 mg (10 mm) |
| pH 1 | 49.5 mg (6 mm) | 362.0 mg (14 mm) |

Volume change in parenthesis (mm)

The product was found to swell at pHI to 7. The product was mixed with 50% HPMC as described in Example 2. Reaction of a 50 mg sample of this material with 3 cc methanol and 3 ml pH0.1 acid resulted in release of misoprostol by HPLC. (100% released in the first hour) reaction of a 50 mg sample with 3 cc methanol and 3 cc pH7 water resulted in 1.73% release in first hour.

EXAMPLE 30

Example 21 was followed but instead of using 10 mole % of α,α'dichloro-p-xylene 17 mole % was utilized. Thus, 3 g of the misoprostol-bound polyamine in 7.12 ms of THF was reacted with 0.414 gms of α,α'-dichloro-p-xylene for 54 hours. After cleanup (following the procedure of Example 21) the elemental analysis was as follows:

%C, 73.91; %H, 11.01
%N, 4.65; %Cl, 4.65

The material was methylated as in Example 23:
%C, 65.58; %H, 10.92; %N, 4.09; %Cl, 10.39
Swelling data:

| | Weight Before Swelling | | Weight After Swelling | |
|---|---|---|---|---|
| | Example 21<br>10 Mole % | 17 Mole % | | |
| | Cross-linker | Cross-linker | 10 Mole % | 17 Mole % |
| pH 1 | 49.7 mg | 50.6 mg | 252.8 mg | 242.6 mg |
| pH 7 | 49.6 mg | 49.5 mg | 541.1 mg | 362.0 mg |

Reaction of 50 mg of this material with 3 cc of methanol and 3 cc pH 1 acid resulted in release of misoprostol.

EXAMPLE 31

The procedure of Example 29 was employed. Thus 2.21 gms misoprostol-bound polyamine (7.45 gms of 29.63 wt. % solution in THF) was weighed into a 100 ml round bottom flask. Then, 0.25 g (0.00103 moles) of 1,6 dibromohexane in 1 cc THF was added with stirring. Then cross-linking reaction was conducted for 54 hours. Cleanup was performed as in Example 21 Elemental analysis: %C, 73.12; %H, 11.63; %N, 4.97; % Br, 5.92.

The cross-linked polyamine was methylated as in Example 22. Elemental Analysis: %C, 64.939; %H, 11.38; %N, 4.06; %Br, 2.53; %Cl, 9.74.

| Swelling data: | Before mg (mm) | After mg (mm) |
|---|---|---|
| pH 1 | 48.8 mg (6 mm) | 296.8 mg (14 mm) |
| pH 7 | 49.5 mg (6 mm) | 910.1 mg (22 mm). |

What is claimed is:

1. A process for preparing a controlled functional density polyamine containing tertiary amine groups and secondary amine groups, and residual unsaturation comprising:

(a) hydroformylating an olefinic-containing polymer in the presence of a suitable hydroformylation catalyst, carbon monoxide and hydrogen wherein hydrogen and carbon monoxide are mixed with said polymer in a $H_2/CO$ molar ratio from about 1:3 to about 3:1 to form a controlled functional density polyaldehyde containing residual unsaturation, and (b) reductively aminating said polyaldehyde with a mixture of a secondary amine and a primary amine in the presence of a suitable reductive amination catalyst and a hydrogen source to form said polyamine wherein said total polyamine functional density is about 10% to about 80% and wherein said tertiary amine groups are derived from said secondary amine and said secondary amine groups are derived from said primary amine.

2. The process of claim 1 wherein said olefinic-containing polymer is selected from the group consisting of polybutadiene and poly(ethylenepropylenediene monomer).

3. The process of claim 1 wherein the function density of aldehyde groups in said polyaldehyde is controlled by controlling the consumption of carbon monoxide and hydrogen during said hydroformylation.

* * * * *

UNITED STATES PATENT AND TRADEMARK OFFICE
CERTIFICATE OF CORRECTION

PATENT NO. : 5,693,319
DATED : December 2, 1997
INVENTOR(S) : Samuel J. Tremont It is certified that error appears in the above-identified patent and that said Letters Patent are hereby corrected as shown below:

Column 6, line 13, "trifluorgcetyl" should read --trifluoracetyl--.
Column 14, line 22, "cross-lined" should read --cross-linked--.
Table 2, example 13, "H NMR after 11294 transients showed <90% olefin" should read --H NMR after 11294 transients showed trace aldehyde and <90% olefin--.

Signed and Sealed this

Seventeenth Day of April, 2001

NICHOLAS P. GODICI

Attest:

Attesting Officer    Acting Director of the United States Patent and Trademark Office